United States Patent [19]

Baumann et al.

[11] 4,172,836

[45] Oct. 30, 1979

[54] IMIDYL COMPOUNDS

[75] Inventors: Marcus Baumann, Basel; Vratislav Kvita, Muttenz; Martin Roth, Basel, all of Switzerland; John S. Waterhouse, Cherry Hinton, England

[73] Assignee: Ciba-Geigy Corporation, Ardsley, N.Y.

[21] Appl. No.: 898,748

[22] Filed: Apr. 21, 1978

Related U.S. Application Data

[62] Division of Ser. No. 696,346, Jun. 15, 1976, Pat. No. 4,107,174.

[30] Foreign Application Priority Data

Jun. 18, 1975 [CH] Switzerland ............... 007951/75
Nov. 27, 1975 [CH] Switzerland ............... 015390/75

[51] Int. Cl.$^2$ ............... C07D 207/12; C07D 403/04; C07D 403/10
[52] U.S. Cl. ............... 260/326.26; 260/326 E; 260/326 N; 260/326.27; 260/326.26; 260/326.4; 260/326.4; 260/326.5 A; 260/326.5 B; 260/326.5 FM
[58] Field of Search ............... 260/326.41, 326.43, 260/326.5 FM, 326.42, 326 NS, 326.5 B, 326.4, 326.25, 326.26, 326.27, 326.5 A, 326.36, 326 E, 326 N; 526/263

[56] References Cited

U.S. PATENT DOCUMENTS

| 2,231,905 | 2/1941 | Hanford et al. | 526/263 |
|---|---|---|---|
| 2,686,774 | 8/1954 | D'Alelio | 260/326.5 FM |
| 2,727,021 | 12/1955 | Price | 526/263 |
| 2,743,260 | 4/1956 | Tawney | 260/326.5 FM |
| 2,790,787 | 4/1957 | Tawney | 260/326.43 |
| 2,958,672 | 11/1960 | Goldberg | 260/326.5 FM |
| 3,129,225 | 4/1964 | Shapiro et al. | 260/326.5 FM |
| 3,151,182 | 9/1964 | Alexander | 260/326.5 FM |
| 3,194,812 | 7/1965 | Norman et al. | 260/326.5 FM |
| 3,265,708 | 8/1966 | Stiteler | 260/326.5 FM |
| 3,301,826 | 1/1967 | Tawney | 260/78 UA |
| 3,308,081 | 3/1967 | Glabish | 526/263 |
| 3,318,766 | 5/1967 | Kato et al. | 260/326.43 |
| 3,337,583 | 8/1967 | Knock | 260/326.43 |
| 3,337,584 | 8/1967 | Knock | 260/326.41 |
| 3,397,210 | 8/1968 | Michalowicz | 260/326.5 FM |
| 3,428,651 | 2/1969 | Kato et al. | 260/326.43 |
| 3,465,001 | 9/1969 | Bolhofer et al. | 260/326.41 |
| 3,557,132 | 1/1971 | Hermann et al. | 260/326.5 FM |
| 3,948,941 | 4/1976 | Patton | 260/326.5 FM |
| 4,045,416 | 8/1977 | Robson et al. | 526/263 |

FOREIGN PATENT DOCUMENTS

| 1594934 | 6/1970 | France | 260/326.5 |
|---|---|---|---|
| 128992 | 3/1974 | Japan | 260/326.5 FM |
| 128991 | 4/1974 | Japan | 260/326.5 FM |
| 128993 | 7/1974 | Japan | 260/326.5 FM |
| 5377 | 5/1975 | Japan | 260/326.5 FM |
| 5380 | 5/1975 | Japan | 260/326.5 FM |
| 53760 | 6/1975 | Japan | 260/326.5 FM |
| 5378 | 7/1975 | Japan | 260/326.5 FM |
| 5379 | 9/1975 | Japan | 260/326.5 FM |

*Primary Examiner*—Donald G. Daus
*Assistant Examiner*—Mary C. Lee
*Attorney, Agent, or Firm*—Luther A. R. Hall

[57] ABSTRACT

The imidyl compounds, according to the invention, of the formula I are suitable for the manufacture of polymers which can be crosslinked by light, which polymers can be, for example, polyesters, polyamides, polyamide-imides, polyimides, polyester-polyamides, polyester-amide-imides, polyethers, polyamines, polysaccharides and polysiloxanes. Polymers of this type are suitable for carrying out photochemical processes. Compared with known polymers, the polymers based on the imidyl compounds according to the invention have the advantage that they are photochemically substantially more sensitive. In addition, this sensitivity can also be further increased effectively by a combination with sensitisers.

5 Claims, No Drawings

IMIDYL COMPOUNDS

This is a Divisional of application Ser. No. 696,346, filed on June 15, 1976, now U.S. Pat. No. 4,107,174, issued on Aug. 15, 1978.

The present invention relates to new imidyl compounds and processes for their manufacture.

The new imidyl compounds correspond to the formula I

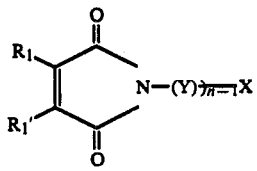

wherein n denotes the number 1 or 2, $R_1$ and $R_1'$ independently of one another denote alkyl with 1-4 carbon atoms or $R_1$ and $R_1'$ conjointly denote a tri- or tetramethylene grouping which is optionally substituted by a methyl group and Y denotes an alkylene group with 1-20 carbon atoms, which optionally contains heteroatoms, a cycloalkylene group with 5 or 6 carbon atoms, an arylene group with 6 to 10 carbon atoms, a

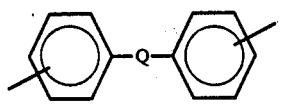

group, in which Q represents a direct bond, —NH—, —O—, —CH$_2$—,

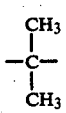

or —OCO—, or denotes an aralkylene group or alkylarylene group with 7 or 8 carbon atoms, and, when n=1, X denotes a group of the formulae

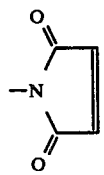

—NH—CO-alkenyl,

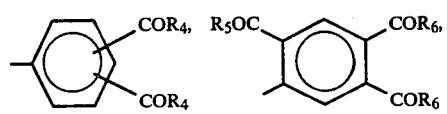

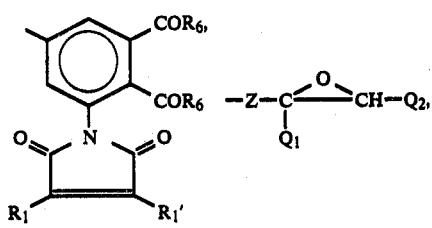

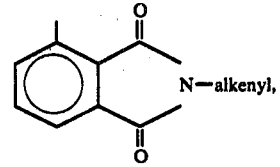

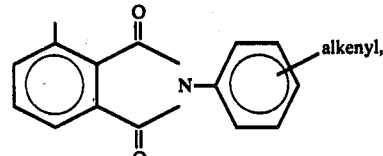

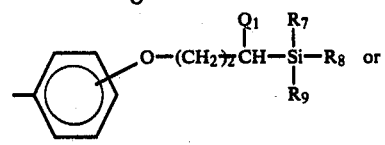

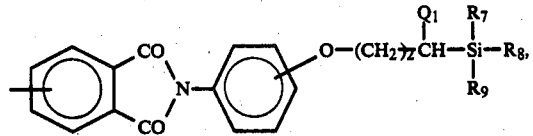

and, when n=2, X denotes halogen, —COOH, —COO$^-$M$^+$, —COO—alkyl, —CN, —CO—O—alkenyl, —O—alkenyl, —O—CO—alkenyl, —NH—alkyl, —NH—alkenyl, —NH—CO—alkenyl, —SH, —S—alkenyl or

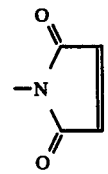

and, when Y represents a cycloalkylene, arylene, aralkylene or alkylarylene group, or a

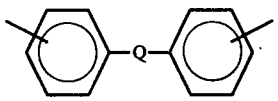

group, according to the definition, X also denotes —OH or —NH$_2$, and $R_2$ and $R_3$ independently of one another denote —OH or —NH$_2$, the two $R_4$'s each denote —OH, —Cl, alkoxy with 1-12 carbon atoms, substituted or unsubstituted phenoxy or —O$^-$M$^+$ or one $R_4$ denotes —OH and the other $R_4$ denotes

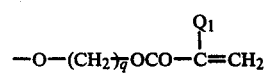

and R₅ denotes —OH, —Cl, alkoxy with 1–12 carbon atoms, unsubstituted or substituted phenoxy or a —O⁻M⁺ group, the two R₆'s have the same meaning as R₄ or the two R₆'s conjointly represent —O—, R₇ and R₈ independently of one another denote hydrogen, —OH, —Cl, —O—alkyl, —O—phenyl, —OCO—alkyl, —OCO—phenyl, —NH—alkyl or

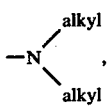

R₉ represents —CH=CH₂, —CH₃, phenyl or the group —O—Si—(CH₃)₃ or R₉ has the same meaning as R₇ or R₈, or R₇ and R₈ conjointly form the group

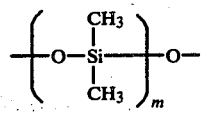

M⁺ denotes an alkali metal cation or a trialkylammonium cation with 3–24 carbon atoms, Z denotes a straight-chain or branched alkylene group with 1–12 carbon atoms, especially the —CH₂— group, Q₁ and Q₂ independently of one another denote hydrogen or methyl, m denotes the number 2, 3 or 4 and q denotes the number 2 or 3 and in the above groups alkyl parts contain 1–8 carbon atoms and alkylene parts contain 2–4 carbon atoms.

Compounds, according to the invention, of the formula Ia

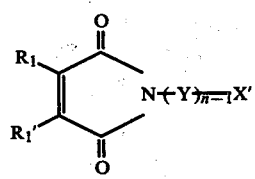
(Ia)

wherein n, R₁, R₁' and Y have the meaning indicated under formula I and, when n=1, X' represents a group of the formulae

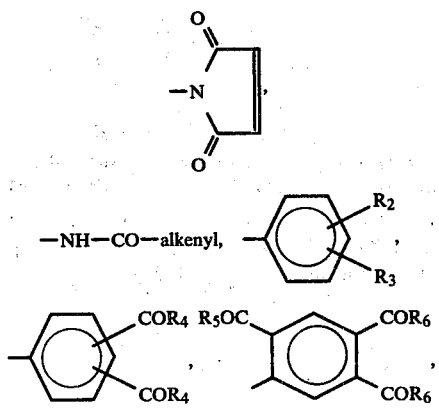

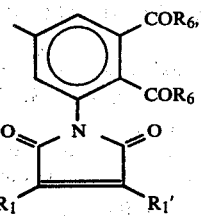

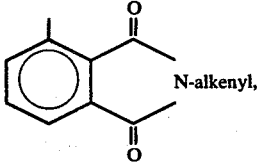

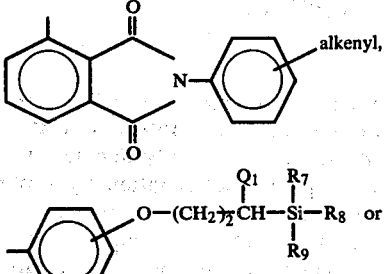

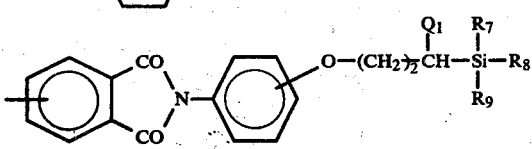

and, when n=2, X' has the same meaning as X and what has been stated under formula I applies in respect of R₂ to R₉, Q, Q₁, M⁺, m, q, alkyl parts and alkylene parts, can be obtained when an amine of the formula II $$H_2N-(Y)_{n-1}X_1 \qquad (II)$$

wherein what has been stated under formula I applies in respect of Y and n and, when n=1, X₁ represents a group of the formulae

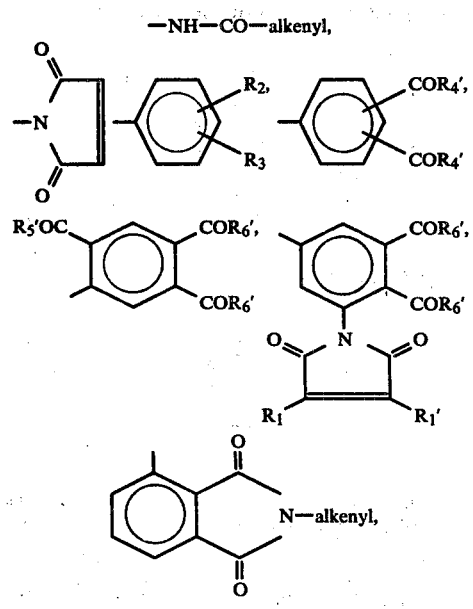

-continued

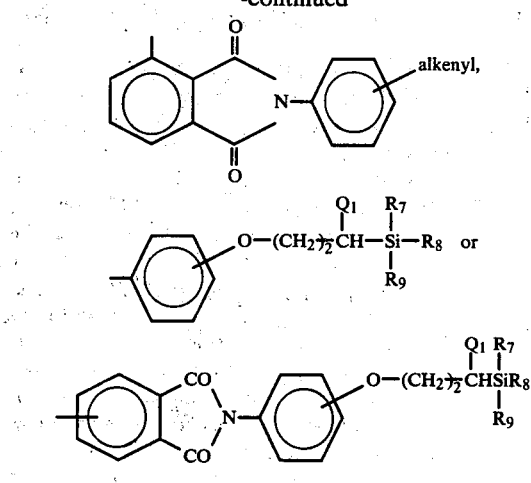

and, when n=2, $X_1$ represents a group corresponding to X' and the two $R_4$''s or the two $R_6$''s each denote —OH, alkoxy with 1-12 carbon atoms, unsubstituted or substituted phenoxy or —O⁻M⁺, or one $R_4'$ or one $R_6'$ denotes —OH and the other $R_4'$ or other $R_6'$ denotes a group

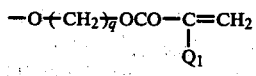

and $R_5'$ denotes —OH, alkoxy with 1-12 carbon atoms, unsubstituted or substituted phenoxy or —O⁻M⁺ and what has been stated under formula I applies in respect of alkenyl groups, $R_1$, $R_1'$, $R_2$, $R_3$, $R_7$, $R_8$, $R_9$, $Q_1$, M⁺, m and q, is reacted, in at least the stoichiometric amount, with an anhydride of the formula III

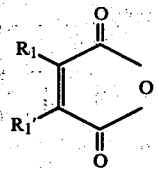

wherein $R_1$ and $R_1'$ have the meaning indicated under formula I, and the resulting compounds are optionally converted into derivatives, according to the definition, of the formula Ia.

According to a modified procedure, compounds, according to the invention, of the formula Ib

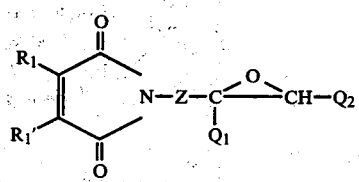

can be manufactured when a compound of the formula IIIa

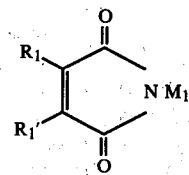

is reacted, in at least the stoichiometric amount, with a halide of the formula IV

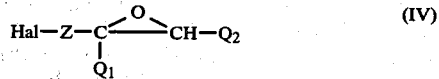

In the above formulae Ib, IIIa and IV, $R_1$, $R_1'$, Z, $Q_1$ and $Q_2$ have the meaning indicated under formula I; $M_1$ represents an alkali metal, especially sodium or potassium, and Hal denotes bromine and, above all, chlorine.

According to the process of the invention—in contrast to analogous reactions with maleic anhydride and phthalic anhydride—the anhydrides of the formula III can be reacted direct with the compounds of the formula II, that is to say without additional measures, such as treatment with agents which eliminate water, to give imidyl derivatives of the formula Ia.

Moreover, the imidyl derivatives of the formula I are obtained, by the process according to the invention, in good to very good yields and are distinguished by a high stability towards acids and bases.

Alkylene, cycloalkylene, arylene, aralkylene, alkylarylene or bicyclic, non-condensed, carbocyclic-aromatic groups according to the definition, which are represented by Y, can be unsubstituted or substituted by, for example, alkyl and alkoxy groups with 1-4 carbon atoms, nitro groups or halogen atoms, such as chlorine, bromine or flourine.

Alkylene groups Y can be straight-chain or branched and can contain one or more hetero-atoms, especially S or O atoms. Unsubstituted alkylene groups with 1 to 12 and in particular 2-6 carbon atoms, such as the methylene group, the 1,2- or 1,1-ethylene group, the 1,3- or iso-propylene group, the 2,2-dimethylpropylene group or the hexamethylene, octamethylene or dodecamethylene group, are preferred.

Preferred cycloalkylene grups are unsubstituted cyclopentylene and, above all, unsubstituted cyclohexylene groups.

Examples of suitable arylene groups Y are the 1,2-, 1,3- and 1,4-phenylene group, the 1,3-tolylene group, the 3-nitro-1,4-phenylene group and the 1,7- and 2,7-naphthylene group. Unsubstituted phenylene groups are preferred.

Possible aralkylene groups are, in particular, the benzylene group and the 2-phenylethylene group.

If Y represents a bicyclic, non-condensed, carbocyclic-aromatic group, the latter is, for example, the 2,2'-biphenylylene group or the 4,4'-diphenylmethane, 4,4'-diphenylamine or 4,4'-diphenyl ether group.

Particularly preferentially, Y represents an unsubstituted alkylene group with 2-6 carbon atoms or the 1,4-cyclohexylene group.

Alkyl or alkoxy groups according to the definition and also alkyl or alkenyl parts of substituents according to the definition can also be straight-chain or branched.

Examples which may be mentioned of alkyl, alkoxy and alkenyl groups according to the definition are: the methyl, ethyl, propyl, isopropyl, n-butyl, tert.-butyl, n-hexyl, methoxy, ethoxy, n-propoxy, isopropoxy, n-butoxy, tert.-butoxy, hexyloxy, octoxy, decyloxy, dodecyloxy, vinyl, allyl, methacryl and crotyl group.

$R_1$ and $R_1'$ preferably have the same meaning. Compounds of the formula I wherein $R_1$ and $R_1'$ each represent the methyl group are very particularly preferred.

If X denotes a halogen atom, the latter is bromine or iodine, but especially chlorine.

If $R_4$ to $R_6$ or $R_4'$ to $R_6'$ represent substituted phenoxy groups, the latter are, in particular, phenoxy groups which are substituted by nitro groups, alkyl or alkoxy groups with 1 or 2 carbon atoms, or halogen atoms, such as chlorine or fluorine, such as the 2-, 3- or 4-nitrophenoxy group, the 2,4- or 3,5-dinitrophenoxy group, the 3,5-dichlorophenoxy group, the pentachlorophenoxy group or the 2-methyl- or 2-methoxy-phenoxy group. Unsubstituted phenoxy groups are preferred.

If n is the number 2, X preferably represents —OH, —COOH, —COO$^-$M$^+$, wherein M$^+$=an alkali metal cation, especially Na, —CO—O—alkenyl, —O—alkenyl, —OCO—alkenyl, —NH$_2$ or —NHCH$_3$.

When n=1, preferred groups X are:

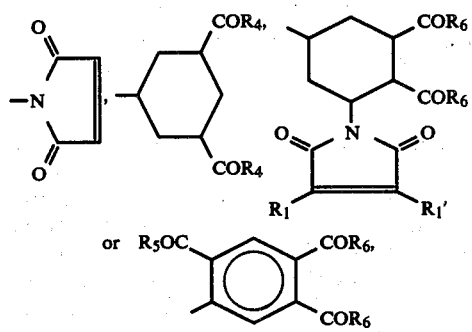

and especially those groups in which one $R_4$ or one $R_6$ denotes —OH and the other denotes

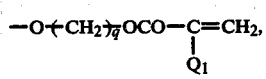

or a group

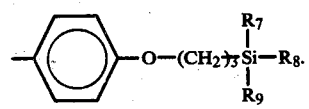

M$^+$ represents, for example, the lithium, sodium, potassium, trimethylammonium, triethylammonium or methyldiethylammonium cation or the tri-n-octylammonium cation. M$^+$ preferably represents the sodium cation.

The compounds of the formulae II, III, IIIa and IV are known or can be manufactured in a manner which is in itself known.

Amines of the formula H$_2$N—Y—O—alkenyl, H$_2$N—Y—S—alkenyl and H$_2$N—Y—NH—alkenyl or H$_2$N—Y—Y—NH—CO—alkenyl and H$_2$N—Y—O—CO—alkenyl can be obtained, for example, by reacting corresponding aminoalcohols, aminomercaptans or diamines, in the presence of bases, such as K$_2$CO$_3$, triethylamine or pyridine, with alkenyl halides, especially alkenyl bromides, or alkenyl acid chlorides respectively.

Amines of the formula H$_2$N—Y—CO—O—alkenyl can be manufactured by reacting corresponding aminoacids, or salts thereof, with alkenyl halides, especially alkenyl bromides.

Aminobenzene-dicarboxylic and -tricarboxylic acids and their derivatives, wherein $R_4'$ or $R_6'$ represent —OH, —Cl, alkoxy or phenoxy or —O$^-$M$^+$, can be employed as such or can be manufactured in situ by reducing the corresponding nitrobenzene-dicarboxylic or -tricarboxylic acids, or derivatives thereof, and used further without intermediate isolation.

Amines of this type, wherein $X_1$ denotes a benzenedicarboxylic or -tricarboxylic acid radical, are preferably used in the form of esters and especially in the form of salts, above all as sodium salts.

Aminobenzene-dicarboxylic and -tricarboxylic acid derivatives, wherein one $R_4'$ or, respectively, one $R_6'$ represents a group

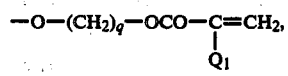

are obtained by reacting the corresponding anhydride with an alkenyl alcohol.

The reaction of the amines of the formula II with the anhydrides of the formula III can be carried out in the melt by heating the reactants to temperatures of up to about 250° C., or also in an aqueous, aqueous-organic or organic medium, in which case the reaction is carried out, depending on the reactants, at temperatures between about 0° C. and the boiling point.

Appropriately, the anhydride of the formula III is employed in the stoichiometric amount or in a slight excess over the amine of the formula II, for example in an up to about 20% molar excess.

Examples of suitable organic solvents are: optionally halogenated aliphatic or aromatic hydrocarbons, such as methylene chloride, chloroform, carbon tetrachloride, 1,1,2-trichloroethane, 1,2-dichloroethylene, benzene, toluene and chlorobenzene; anhydrous acetic acid; aliphatic and cycloaliphatic ketones, such as acetone, methyl ethyl ketone, cyclopentanone and cyclohexanone; cyclic ethers, such as tetrahydrofurane, tetrahydropyrane and dioxane; cyclic amides, such as N-methyl-2-pyrrolidone, N-acetyl-2-pyrrolidone and N-methyl-β-caprolactam; N,N-dialkylamides of aliphatic monocarboxylic acids with 1–3 carbon atoms in the acid part, such as N,N-dimethylformamide, N,N-dimethylacetamide, N,N-diethylacetamide and N,N-dimethyl-methoxyacetamide; alkyl esters of aliphatic monocarboxylic acids with a total of 2–6 carbon atoms, such as formic acid methyl, ethyl or n-butyl ester or acetic acid methyl, ethyl or n-butyl ester; hexamethylphosphoric acid triamide (hexametapol); N,N,N',N'-tetramethylurea; tetrahydrothiophene dioxide (sulpholane); and dialkylsulphoxides, such as dimethylsulphoxide and diethylsulphoxide.

Mixtures of solvents of this type can also be employed. Preferred solvents are dioxane, anhydrous acetic acid, methylene chloride, benzene, toluene, xylene, ethyl acetate, methyl ethyl ketone and chlorobenzene.

The reaction of the alkali metal salts of the formula IIIa with the halides of the formula IV is also carried out in a manner which is in itself known, appropriately in suspension or in a suitable organic solvent and optionally in the presence of a salt of a quaternary base, such as tetramethylammonium chloride. Polar solvents, such as alcohols, acetone, acetonitrile, N,N-dimethylformamide and dimethylsulphoxide, are preferred.

The compounds of the formula Ia, which have been manufactured according to the invention, can, if desired—and depending on the nature of the amines of the formula II which have been used—be converted in a manner which is in itself known into other compounds, according to the definition, of the formula Ia, or into derivatives thereof. Examples which may be mentioned are:

(1) X′=—COCl (derivative) and R₄ to R₆=—Cl

By reaction of compounds of the formula Ia, wherein X′=—COOH and R₄ to R₆=—OH or —O⁻M⁺, or the two R₆'s conjointly =—O—, with suitable chlorinating agents, such as thionyl chloride, oxalyl chloride and phosgene.

(2) X′=—COOH and R₄ to R₆=—OH

By hydrolysis of compounds of the formula Ia, wherein X′=—COO⁻M⁺, —COO-alkyl or —CN, or of compounds of the formula Ia, wherein R₄ to R₆=—O⁻M⁺, alkoxy or phenoxy or the two R₆'s conjointly=—O—, in an acid or alkaline medium, or by alcoholysis of compounds of the formula Ia, wherein X′=—CN, in an acid medium to give the corresponding imino-ether and subsequent hydrolysis of the latter.

(3) X′=—COO—alkyl and R₄ to R₆=alkoxy or phenoxy

By reaction of compounds of the formula Ia, wherein X′=—COOH or —COCl and R₄ to R₆=—OH or —Cl, or the two R₆'s conjointly=—O—, with corresponding alcohols, or by transesterification of compounds of the formula Ia, wherein X′=—COO-alkyl and R₄ to R₆=alkoxy or phenoxy.

(4) X′=—NH₂ or —NH-alkyl

By catalytic reduction of compounds of the formula Ia, wherein X′=—CN, and, optionally, subsequently alkylation of the reaction product.

(5) X′=—SH

By treatment of compounds of the formula Ia, wherein X′=halogen, with suitable sulphur compounds, such as thiourea or Na₂S.

(6) X′=—O-alkenyl, —NH-alkenyl or —S-alkenyl

By reaction of compounds of the formula Ia, wherein X′=—OH, —NH₂ or —SH, with alkenyl halides, especially bromides, in the presence of bases, such as K₂CO₃.

(7) X′=—O-CO-alkenyl

By reaction of compounds of the formula Ia, wherein X′=—OH, with corresponding unsaturated acids, acid chlorides or esters.

(8) X′=—CO—O-alkenyl

By reaction of compounds of the formula Ia, wherein X′=—COOH (or —COCl), with corresponding unsaturated esters or alcohols in the presence of acids or bases.

(9) X′=—NH—CO-alkenyl

By reaction of compounds of the formula Ia, wherein X′=—NH₂, with corresponding acid chlorides.

(10) R₆=

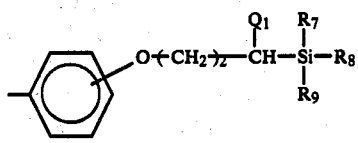

By reaction of compounds of the formula Ia, wherein the two R₆'s conjointly=—O—, with corresponding alcohols.

(11) X′=

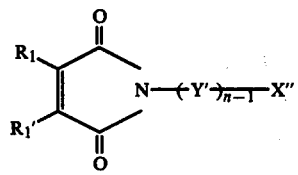

By reaction of compounds of the formula Ia, wherein n=2, Y=phenylene and X′=—OH, with alkenyl halides and subsequent reaction of the product with a compound of the formula

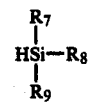

Compounds, which are in themselves known, of the formula Ic

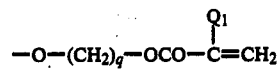

(Ic)

wherein R₁, R₁′ and n have the meaning indicated under formula I, Y represents an alkylene group which optionally contains hetero-atoms and X″ represents —OH or —NH₂, can also be employed for the reactions according to (6), (7) and (9).

Further derivatives of compounds of the formula Ia can be manufactured as follows:

X′=—CO—O—CHO

By reaction of acid chlorides obtained according to (1) with an alkali metal salt of formic acid.

X′=—CO—O—CO—CF₃

By reaction of compounds of the formula Ia, wherein X′=—COOH, with CF₃—CO—O—CO—CF₃.

X′=—CO—O—CO—O—alkyl

By reaction of compounds of the formula Ia, wherein X′=—COO⁻M⁺, with compounds of the formula Cl-CO-O-alkyl.

X'=—CO—NH—CO—alkenyl

By reaction of acid chlorides with alkenyl acid amides.

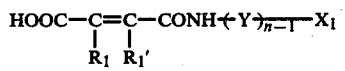

By reaction of acid chlorides or esters with corresponding unsaturated alcohols.

According to another modified process, the amidecarboxylic acid of the formula

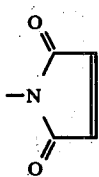

which are formed as intermediates during the reaction of the amines of the formula II with the anhydrides of the formula III, can be isolated in the form of derivatives, for example as salts, and subsequently cyclised, chemically or by means of heat, in a known manner to give compounds of the formula I.

Compounds of the formula I, wherein X represents a group

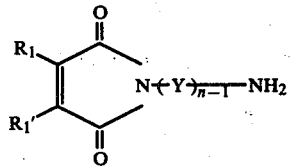

can also be obtained by reacting a compound, which is in itself known, of the formula IIIb

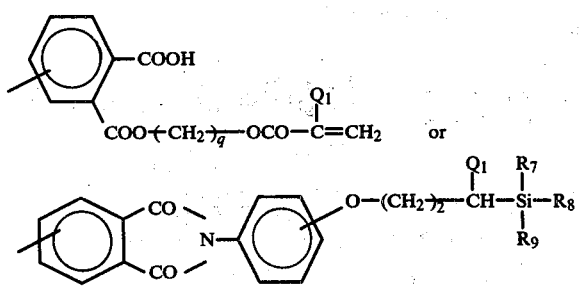

with maleic anhydride.

Furthermore, compounds of the formula I wherein, when n=1, X represents a group of the formula

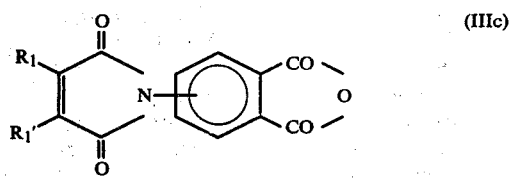

can be obtained by reacting an anhydride of the formula IIIc

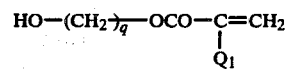

(manufactured by reacting 3- or 4-aminophthalic acid with an anhydride of the formula III) with an alcohol of the formula

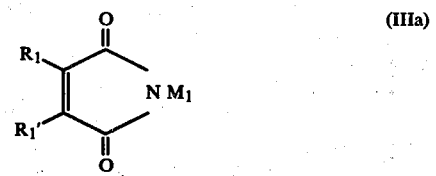

or with an aminophenol and subsequently further converting the resulting reaction product, as indicated under (11).

Finally, compounds, according to the invention, of the formula I, wherein X represents a —OH, —NH$_2$ or —NH-alkyl group, can also be obtained according to another modified process by reacting a compound of the formula IIIa

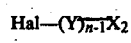

wherein R$_1$ and R$_1'$ have the abovementioned meaning and M$_1$ represents an alkali metal, especially sodium or potassium, with a halide of the formula Hal—(Y)$_{n-1}$X$_2$ wherein Y and n have the meaning indicated under formula I and X$_2$ denotes —OH, —NH$_2$ or —NH—alkyl.

When the reaction has ended, the compounds of the formula I are isolated in a customary manner, for example by filtration or by stripping off the solvent, and are purified if necessary, for example by washing with water, recrystallising from suitable solvents, such as methanol, ethanol, benzene or toluene, or by sublimation or distillation.

After the reaction with the anhydride of the formula III, compounds of the formula I, wherein X represents a group

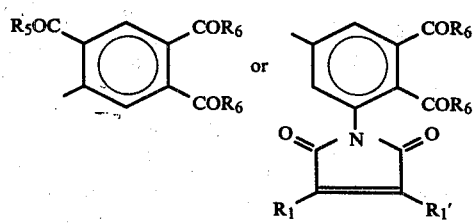

and the R$_6$ each represent —OH or —O⁻M⁺, can, in a manner which is in itself known, be cyclised chemically, that is to say using dehydrating agents, such as acetic anhydride, and/or by the action of heat.

The compounds, according to the invention, of the formula I and the abovementioned derivatives are suitable for the manufacture of polymers which are crosslinkable under the influence of electromagnetic waves, especially light, such as polyesters, polyamides, polyamide-imides, polyimides, polyester-polyamides, polyester-amide-imides, polyethers, polyamines, gelatine, polysaccharides and polysiloxanes. Crosslinkable polymers of this type can be manufactured, for example, by incorporating compounds of the formula I into suitably substituted polymers, such as polyvinyl alcohols, polyanhydrides or polyethers, or by polycondensation with diamines, diols or aminoalcohols or derivatives thereof and optionally in the presence of further di-, tri- or tetracarboxylic acid derivatives.

Crosslinkable polyethers can, for example, also be obtained by a polyaddition reaction of compounds of the formula I with oxides, such as ethylene oxide, propylene oxide and styrene oxide, optionally in the presence of amines, alcohols or phenols.

Finally, crosslinkable polymers can also be obtained by homopolymerisation of compounds of the formula I or, preferably, by copolymerisation of such compounds with vinyl comonomers, such as vinyl chloride, vinylidene chloride, vinyl acetate, styrene, acrylic acid derivatives and methacrylic acid derivatives or acrylonitrile.

A number of polymers which can be crosslinked under the action of light are already known. In most of these light-sensitive polymers the photo-active groups are linked as sidechain substituents to the polymer chain. In this context, the following Japanese Offenlegungsschriften should be mentioned in particular: Japanese Application 49/128,991, Japanese Application 49/128,992, Japanese Application 49/128,993, Japanese Application 50/5,376, Japanese Application 50/5,377, Japanese Application 50/5,378, Japanese Application 50/5,379 and Japanese Application 50/5,380.

In these Japanese patent applications processes for the manufacture of light-sensitive polymers are claimed and these polymers contain, as light-sensitive groups, groups of the formula II

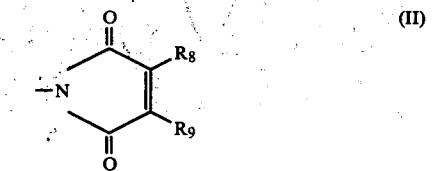

in which $R_8$ denotes an aromatic radial and $R_9$ denotes H, halogen, alkyl or —CN.

However, known polymers of this type have the disadvantage that their photochemical sensitivity is much too low for special phototechnical application. This characteristic has a negative effect, especially in that, ultimately, unsharp images or relief images result when corresponding photomechanical processes are carried out and that the exposure times required are too long.

In the case of these polymers it is also not possible to eliminate this disadvantage by using sensitisers for photochemical reactions. That is to say, these known light-sensitive polymers evidently completely prevent these sensitisers from displaying their action.

The imidyl compounds according to the invention now, surprisingly, lead to polymers which do not display the disadvantages of the known light-sensitive polymers. Thus, they display a greater sensitivity towards electromagnetic waves and, in addition, this sensitivity can also be further increased by a combination with sensitisers.

Crosslinkable polymers of this type are used, for example, as a photoresist, for the manufacture of photographic materials on the basis of non-silver processes or for the manufacture of printing plates. They are distinguished by high sensitivity to light and good quantum yields.

EXAMPLE 1

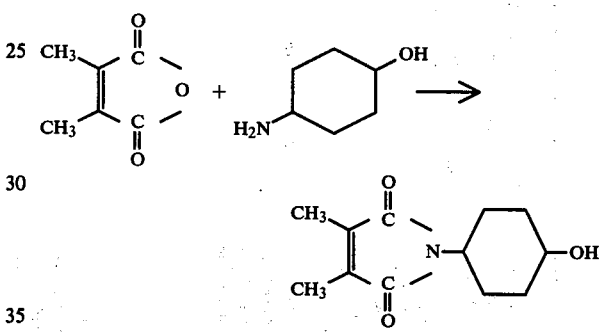

126 g (1 mol) of dimethylmaleic anhydride and 115 g (1 mol) of 4-aminocyclohexanol are warmed, whilst stirring, to 120°–125° C. (internal temperature) for 30 minutes in an oil bath. After cooling to about 20° C., the reaction product is dissolved in 500 ml of methylene chloride and the solution is extracted once with 100 ml of 1 N NaOH, whilst cooling with ice. The reaction product is then washed twice with water and dried over Na$_2$SO$_4$. The solvent is evaporated and the residue is recrystallised from a 1:1 mixture by volume of ethyle acetate and petroleum ether. 155 g (70% of theory) of N-(4-hydroxycyclohexyl)-dimethyl-maleimide are obtained; melting point 109°–111° C.

Analysis for C$_{12}$H$_{17}$NO$_3$ (molecular weight 223.3): calculated: C 64.6%, H 7.5%, N 6.3%, O 21.5%: found: C 64.5%, H 7.5%, N 6.3%, O 21.6%.

NMR (CHCl$_3$): signal for the methyl protons at 1.95 ppm.

Table I which follows indicates further compounds of the formula I which have been prepared according to the procedure described in Example 1 above, by reacting 2,3-dimethylmaleic anhydride with the amines listed.

Table I

Examples 2-8

| Example No. | Compound of the formula I | Compound of the formula II | Compound of the formula III | Reaction time minutes | Temperature °C | re-crystallised from | Melting point °C | Yield % of theory | NMR** (DMSO-$\delta$ in p |
|---|---|---|---|---|---|---|---|---|---|
| 2 | CH₃-CO-N(-OH-phenyl)-CO-CH₃ (dimethylmaleimide with 2-hydroxyphenyl) | 2-aminophenol (NH₂, OH) | 2,3-dimethyl-maleic anhydride | 60 | 140 | methanol | 161–162 | 75 | 2.0 |
| 3 | dimethylmaleimide with 2-aminobiphenyl | 2-amino biphenyl (NH₂, with phenyl) | 2,3-dimethyl-maleic anhydride | 30 | 150 | ethanol | 206 | 55 | 1.9 |
| 4 | dimethylmaleimide with 4-aminophenyl-NH₂ | p-phenylenediamine (H₂N–C₆H₄–NH₂) | 2,3-dimethyl-maleic anhydride | 45 | 180 | methanol | 138–139 | 50 | 1.95* |
| 5 | dimethylmaleimide with 4-COOH-phenyl | 4-aminobenzoic acid (H₂N–C₆H₄–COOH) | 2,3-dimethyl-maleic anhydride | 15 | 200 | ethanol | 227–230 | 50 | 1.95 |
| 6 | dimethylmaleimide with 6-hydroxy-2-naphthyl | 6-amino-2-naphthol | 2,3-dimethyl-maleic anhydride | 30 | 200 | ethanol/H₂O | 210–212 | 52 | 1.95 |
| 7 | dimethylmaleimide with hydroxy-naphthyl | amino-naphthol | 2,3-dimethyl-maleic anhydride | 30 | 250 | tetrahydrofurane/H₂O | 232–237 | 32 | 2.0 |
| 8 | dimethylmaleimide with 4-(CH₂)₂OH-phenyl | 4-(2-hydroxyethyl)aniline (H₂N–C₆H₄–CH₂CH₂OH) | 2,3-dimethyl-maleic anhydride | 30 | 130 | ethyl acetate | 115–116 | 40 | 2.0* |

*(CDCl₃)
**Methyl protons of the dimethylmaleimidyl radical

EXAMPLE 9

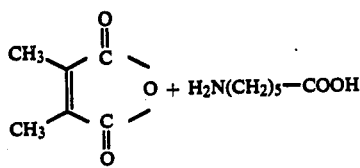

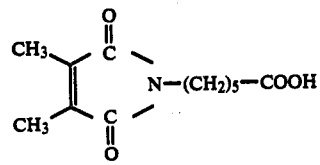

145 g (1.15 mols) of dimethylmaleic anhydride and 150 g (1.15 mols) of ε-amino-caproic acid are dissolved in 700 ml of anhydrous acetic acid and the solution is boiled under reflux for 8 hours. The acetic acid is then distilled off in a rotary evaporator. The residue is dissolved in 500 ml of diethyl ether and the solution is washed once with 100 ml of 1 N NaOH, whilst cooling with ice, and twice with water. After drying over $Na_2SO_4$ and evaporating the diethyl ether, the residue is crystallised from about 150 ml of isopropyl ether. 209 g (76% of theory) of N-(caproic acid)-dimethylmaleimide are obtained; melting point 43°–45° C.

Analysis for $C_{12}H_{17}NO_4$ (molecular weight 239.3): calculated: C 60.2%, H 7.2%, N 5.9%, O 26.8%: found: C 60.3%, H 7.2%, N 5.9%, O 26.9%.

NMR ($CHCl_3$): signal for the methyl protons at 2.0 ppm.

Table II which follows indicates further compounds of the formula I which were prepared according to the procedure described in Example 9 above, by reacting 2,3-dimethylmaleic anhydride with the amines listed.

Table II

Examples 10–16

| Ex. No. | Compound of the formula I | Compound of the formula II | Compound of the formula III | Reaction time hours | Temperature °C. | Solvent | re-crystal-lised from | Melting point/boiling point °C. | Yield % of theory | NMR (CDCl₃) δ in ppm |
|---|---|---|---|---|---|---|---|---|---|---|
| 10 | CH₃–CO\N–(CH₂)₂COOH / CH₃–CO | H₂N(CH₂)₂COOH | 2,3-dimethyl-maleic anhydride | 8 | reflux | anhydrous acetic acid | ethyl acetate/petroleum ether | 83–86 | 66 | 1.95 |
| 11 | CH₃–CO\N–CH–COOH\CH₂CH₂S—CH₃ / CH₃–CO | H₂N—CH—COOH\CH₂CH₂S—CH₃ | 2,3-dimethyl-maleic anhydride | 5 | reflux | anhydrous acetic acid | iso-propyl ether | 101–102 | 70 | 2.0 |
| 12 | CH₃–CO\N–CH–COOH\CH₃ / CH₃–CO | H₂N—CH—COOH\CH₃ | 2,3-dimethyl-maleic anhydride | 16 | reflux | anhydrous acetic acid | methanol | 164–165 | 40 | 1.9 |
| 13 | CH₃–CO\N–(C₆H₄)–OH / CH₃–CO | H₂N–(C₆H₄)–OH | 2,3-dimethyl-maleic anhydride | 2 | reflux | anhydrous acetic acid | methanol | 200 | 95 | 2.0** |
| 14 | CH₃–CO\N–CH₂—COOH / CH₃–CO | H₂N—CH₂—COOH | 2,3-dimethyl-maleic anhydride | 3 | reflux | anhydrous acetic acid | ethyl acetate | 162–164 | 30 | 2.0 |
| 15 | CH₃–CO\N–(CH₂)₂NHCH₃ / CH₃–CO | H₂N(CH₂)₂NHCH₃ | 2,3-dimethyl-maleic anhydride | 1 | reflux | benzene | — | 78° 0.1 mm Hg; melting point 21°–23° | 54 | 2.0 |
| 16 | CH₃–CO\N–(C₆H₄)–CH₂OH / CH₃–CO | H₂N–(C₆H₄)–CH₂OH | 2,3-dimethyl-maleic anhydride | 1 | 25 | ethyl acetate | water | 83–85 | 60 | 2.0 |

*methyl protons of the dimethylmaleimidyl radical
**DMS.-d₆

EXAMPLE 17

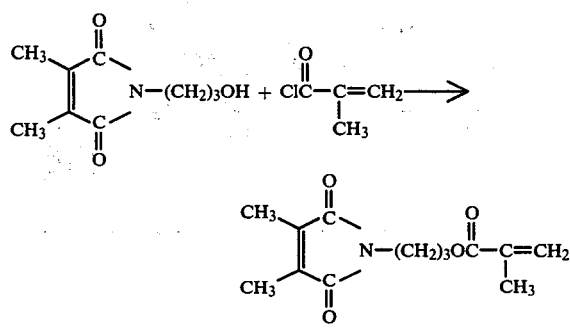

183.0 g (1.0 mol) of N-(3-hydroxypropyl)-dimethylmaleimide (obtained by reacting dimethylmaleic anhydride with 1,3-aminopropanol) and 111.3 g (1.1 mols) of triethylamine (dried over NaOH) are dissolved in 400 ml of diethyl ether (dried over Na) in a 750 ml sulphonation flask, which is fitted with a dropping funnel, with a pressure equalising device, a condenser and a thermometer, and the solution is cooled to 0° C. 104.5 g (1.0 mol) of methacrylic acid chloride are added dropwise to this solution at such a rate that the temperature does not exceed 10° C.

When the reaction has ended, the reaction mixture is stirred until it has warmed to room temperature (20°–25° C.).

The triethylamine hydrochloride which has precipitated during the reaction is now separated from the remaining reaction solution by filtration. The ether extract is washed with slightly acidified water until neutral, dried over Na sulphate and then concentrated in vacuo without heating.

224.1 g (89.3% of theory) of the above imidyl derivative are obtained; $n_{20}^d = 1.4962$.

Analysis for $C_{13}H_{17}O_4N$ (molecular weight 251): calculated: C 62.1%, H 6.8%, N 5.6%: found: C 62.3%, H 7.0%, N 5.4%.

NMR spectrum ($CDCl_3$): $\delta = 1.95$ ppm (methyl protons of the dimethylmaleimidyl radical).

EXAMPLE 18

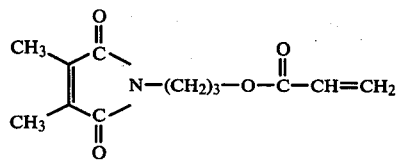

If, in Example 17, the equivalent amount of acrylic acid chloride is used in place of 104.5 g (1.0 mol) of methacrylic acid chloride and the procedure is otherwise identical, 214.7 g (90.4% of theory) of the above imidyl derivative are obtained; $n_{20}^d = 1.4966$.

Analysis for $C_{12}H_{15}O_4N$ (molecular weight 237): calculated: C 59.2%, H 5.9%, N 6.3%: found: C 58.8%, H 5.9%, N 6.0%.

NMR spectrum ($CDCl_3$): $\delta = 1.95$ ppm (methyl protons of the dimethylmaleimidyl radical).

Table III which follows indicates further compounds of the formula I, which were obtained according to the procedure described in Example 17 by reacting N-(2-hydroxyethyl)-dimethylmaleimide (Examples 19 and 20), N-(2-hydroxypropyl)-dimethylmaleimide (Example 21), N-(6-hydroxy-n-hexyl)-dimethylmaleimide (Example 22), N-(4-hydroxycyclohexyl)-dimethylmaleimide (Examples 23 and 24) and N-(6-hydroxy-n-hexyl)-tetrahydrophthalimide (Example 25) with methacrylic acid chloride or acrylic acid chloride.

Table III
Examples 19–25

| Example No. | Compound of the formula I | Yield % of theory | Analysis calculated C % | H % | N % | found C % | H % | N % | NMR (CDCl₃) = ppm* | $n^d_{20}$ |
|---|---|---|---|---|---|---|---|---|---|---|
| 19 | CH₃–CO–N((CH₂)₂–OCO–C(CH₃)=CH₂)–CO–CH₃ (dimethylmaleimide) | 91.4 | 60.8 | 6.4 | 5.9 | 60.6 | 6.6 | 5.3 | 1.95 | 1.4965 |
| 20 | CH₃–CO–N((CH₂)₂–OCO–CH=CH₂)–CO–CH₃ | 89.9 | 59.2 | 5.9 | 6.3 | 58.8 | 5.9 | 6.0 | 1.95 | 1.4966 |
| 21 | CH₃–CO–N(CH₂CH(CH₃)–OCO–C(CH₃)=CH₂)–CO–CH₃ | 92.1 | 62.1 | 6.8 | 5.6 | 62.6 | 6.9 | 4.5 | 1.95 | 1.4961 |
| 22 | CH₃–CO–N((CH₂)₆–OCO–C(CH₃)=CH₂)–CO–CH₃ | 90.2 | 65.5 | 7.9 | 4.8 | 65.3 | 8.0 | 4.6 | 1.95 | 1.4962 |
| 23 | CH₃–CO–N(cyclohexyl–OCO–C(CH₃)=CH₂)–CO–CH₃ | 82.3 | 65.9 | 7.2 | 4.8 | 65.4 | 6.9 | 4.6 | 1.96 | |
| 24 | CH₃–CO–N(cyclohexyl–OCO–CH=CH₂)–CO–CH₃ | 91.5 | 65.0 | 6.9 | 5.0 | 65.9 | 6.4 | 4.8 | 1.95 | |

Table III-continued

Examples 19-25

| Example No. | Compound of the formula I | Yield % of theory | Analysis calculated C % | H % | N % | Analysis found C % | H % | N % | NMR (CDCl₃) = ppm* | $n^d_{20}$ |
|---|---|---|---|---|---|---|---|---|---|---|
| 25 |  | 89.0 | 67.7 | 7.9 | 4.4 | 66.8 | 7.8 | 4.3 | | 1.5029 |

*methyl protons of the dimethylmaleimidyl radical

EXAMPLE 26

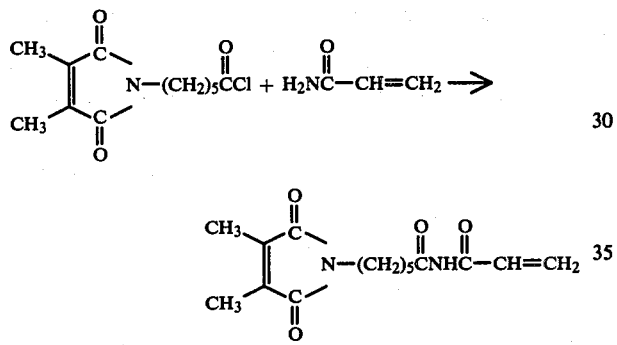

71.0 g (1.0 mol) of acrylic acid amide and 101.25 g of triethylamine, dissolved in 200 ml of anhydrous acetone, are initially introduced into a 1,500 ml sulphonation flask which is fitted with a dropping funnel, with a pressure equalising device, a condenser and a thermometer. 257.5 g (1.0 mol) of N-(caproic acid chloride)-dimethylmaleimide, dissolved in 400 ml of anhydrous acetone, are added dropwise to this solution, whilst cooling with ice/water, at such a rate that the temperature does not exceed 40° C. When the reaction has taken place, the mixture is stirred for 1 hour. The resulting triethylamine hydrochloride is then separated from the remaining reaction solution by filtration. The acetone extract is concentrated in vacuo without heating.

For further working up, the residue is taken up in 1,000 ml of diethyl ether and washed with 4 times 1,000 ml of water. After drying with Na sulphate, the ether phase is concentrated in vacuo without heating. 208.0 g (71.2% of theory) of the above imidyl derivative are obtained; melting point about 20° C.

Analysis for C₁₅H₂₀O₄N₂ (molecular weight 292): calculated: C 61.6%, H 6.8%, O 21.9%, N 9.6: found: C 60.9, H 6.4, O 21.7, 9.5:

NMR spectrum (CDCl₃): δ=1.94 ppm (methyl protons of the dimethylmaleimidyl radical).

The acid chloride used in the above example is obtained in a manner which is in itself known by reacting the N-(caproic acid)-2,3-dimethylmaleimide described in Example 9 with thionyl chloride.

EXAMPLE 27

140.0 g (1.0 mol) of N-amino-dimethylmaleimide and 111.3 g (1.1 mols) of triethylamine (dried of NaOH) are dissolved in 2,500 ml of dichloromethane in a 4,500 ml sulphonation flask, which is fitted with a dropping funnel, with a pressure equalising device, a condenser and a thermometer, and the solution is cooled to 0° C.

104.5 g (1.0 mol) of methacrylic acid chloride are added dropwise to this solution at such a rate that the temperature does not exceed 10° C.

When the reaction has taken place, the mixture is heated to 40° C. and then stirred at this temperature for one hour.

After cooling to about 20°-25° C., the reaction solution is washed with water until neutral. The dichloromethane extract is dried over Mg sulphate and then concentrated to dryness in vacuo without heating. 187.6 g (90.2% of theory) of the above N-[1-aza-3-methyl-2-oxobut-3-enyl]-2,3-dimethylmaleimide are obtained; melting point 105° C.

Analysis for C₁₀H₁₂O₃N (molecular weight 208): calculated: C 57.69%, H, 5.81%, N 13.46%: found: C 57.46%, H 5.69%, N 12.98%:

NMR spectrum (CDCl₃): δ=1.96 ppm (methyl protons of the dimethylmaleimidyl radical).

EXAMPLE 28

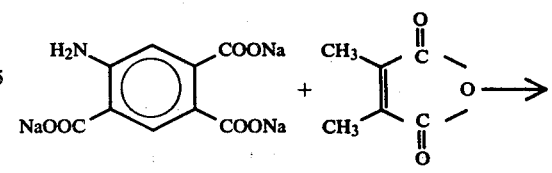

-continued

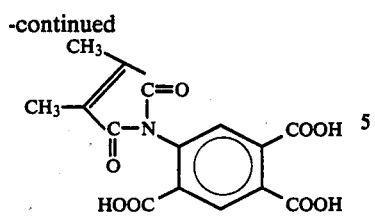

102.05 g (0.4 mol) of 5-nitrotrimellitic acid are suspended in 260 ml of water and 48 g (1.2 mols) of sodium hydroxide dissolved in 240 ml of water are added. The resulting solution is hydrogenated at 42° C. in the presence of 10 g of a palladium-on-charcoal catalyst containing 5% by weight of Pd. The reaction solution is filtered and the filtrate is concentrated to a volume of about 150 ml and first 75 ml of toluene and then 50.44 g (0.4 mol) of dimethylmaleic anhydride are added and the mixture is boiled under reflux for 10 minutes. The reaction mixture is evaporated to dryness, the residue is dissolved in 500 ml of hot water and the solution is acidified with 438 ml of 10% strength hydrochloric acid and cooled to 0°–5° C. and 14 ml of 32% strength hydrochloric acid are added. The precipitate which has separated out is filtered out, rinsed with 50 ml of ice water and dried at 80° C. in a drying cabinet. The yield of 5-dimethylmaleimidyl-trimellitic acid is 111.1 g (83% of theory).

EXAMPLE 29

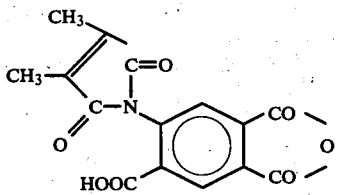

140 ml of acetic anhydride are added to 76.64 g (0.23 mol) of the dimethylmaleimidyl-trimellitic acid prepared according to Example 28 and the mixture is heated to the boil. The acid dissolves completely within a short time. The solution is evaporated to dryness, the residue is boiled with 180 ml of benzene and the precipitate is filtered off and dried at 80° C. in a drying cabinet. 51.8 g (71% ) of 5-dimethylmaleimidyl-trimellitic anhydride are obtained; melting point 181°–185°.

EXAMPLE 30

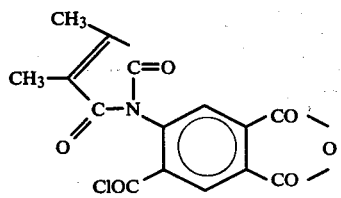

50.43 g (0.16 mol) of the 5-dimethylmaleimidyltrimellitic anhydride prepared according to Example 29 are suspended in 320 ml of benzene, 17.5 ml (0.24 mol) of thionyl chloride and 0.5 ml of N,N-dimethylformamide are added and the mixture is heated to 90° C., whilst stirring. The turbid solution which has formed after boiling for 15 minutes is filtered and the filtrate is cooled. 5-Dimethylmaleimidyltrimellitic anhydride-chloride, which has crystallised out over sodium acetate, is dried at 80° C./0.5 mm Hg. Yield: 29.6 g (55%); melting point 184°–185° C.

Analysis for $C_{15}H_8NO_6Cl$ (molecular weight 333.68): calculated: C 53.99%, H 2.42%, N 4.20%, Cl 10.63%: found: C 53.69%, H 2.39%, N 3.95%, Cl 10.92%.

EXAMPLE 31

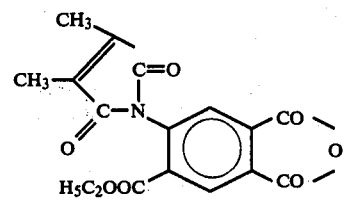

3.33 g (0.01 mol) of the 5-dimethylmaleimidyltrimellitic anhydride-chloride prepared according to Example 30 are dissolved in dioxane. 0.58 mol (0.01 mol) of ethanol are the added dropwise and the reaction mixture is stirred overnight. The reaction mixture is then heated to 85° C. for 15 minutes and cooled and 35 ml of cyclohexane are added slowly. The product which has crystallised out is filtered off, rinsed with 5 ml of cyclohexane and dried at 100° C. in a drying cabinet. 2.49 g (72.5% of theory) of 5-dimethylmaleimidyltrimellitic anhydride-ethyl ester are obtained; melting point 172°–174° C.

Analysis for $C_{17}H_{13}NO_7$ (molecular weight 343.29): calculated: C 59.48%, H 3.82%, N 4.08%: found: C 59.17%, H 3.80%, N 4.25% .

EXAMPLE 32

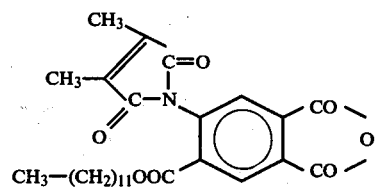

23.35 g (0.07 mol) of the 5-dimethylmaleimidyltrimellitic anhydride-chloride prepared according to Example 30 are dissolved in 70 ml of dioxane, 13.04 g (0.07 mol) of lauryl alcohol, dissolved in 25 ml of dioxane, are added whilst stirring and the mixture is left to stand overnight. The solution is then evaporated.

35 ml of diethyl ether are added to the residue. After stirring for 3 hours, 35 ml of cyclohexane are added to the resulting fine crystalline suspension and the precipitate is filtered off and dried at 50° C., in a drying cabinet. 24 g (71% of theory) of 5-dimethylmaleimidyl-trimellitic anhydride-lauryl ester are obtained; melting point 93° C. Analysis for $C_{27}H_{33}NO_7$ (molecular weight 483.56): calculated: C 67.06%, H 6.88%, N 2.90%: found: C 66.82%, H 6.97%, N 2.98%.

EXAMPLE 33

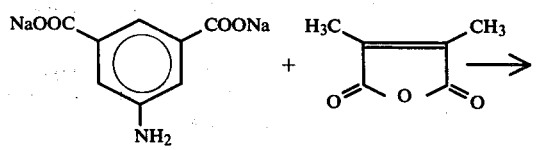

-continued

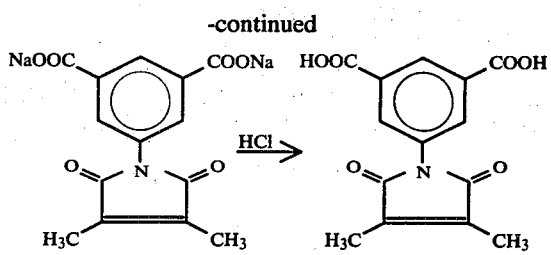

76.5 g (0.34 mol) of disodium 5-amino-isophthalate are dissolved in 200 ml of water at 40°–50° C. in a 1 liter three-necked flask, which is provided with a reflux condenser and a stirrer. 44.2 g (0.35 mol) of dimethylmaleic anhydride, dissolved in 300 ml of dimethylacetamide, are added to this solution, whilst stirring. The slightly yellowish solution is then boiled at 100° C. for 30 minutes, whilst stirring continuously. The solution is then acidified (Congo Blue), at a temperature of 95°–100° C., with 10% strength hydrochloric acid. After the mixture has cooled to room temperature, the resulting precipitate is filtered off. The crude product is dried at 90° C. in vacuo. 68.5 g (70% of theory) of 5-dimethylmaleimidyl-isophthalic acid are obtained; melting point above 250° C.

Analysis for $C_{14}H_{11}NO_6$ (molecular weight 289): calculated: C 59.1%, H 3.8%, N 4.8%: found: C 58.2%, H 4.0%, N 4.9%.

EXAMPLE 34

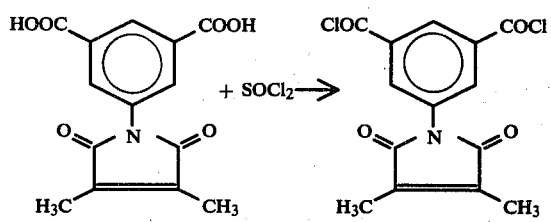

50.9 g (0.176 mol) of 5-dimethylmaleimidyl-isophthalic acid and 500 ml of thionyl chloride was boiled together under reflux, in a 1 liter single-necked flask, which is provided with a reflux condenser, until a clear solution has formed. About 5 drops of pyridine are added in order to catalyse the reaction. The reaction mixture is then evaporated to dryness in a rotary evaporator, an orange-red residue being obtained.

The orange-red residue is then extracted, in a hot extractor, with anhydrous cyclohexane, the acid chloride being obtained. After cooling to 20°–25° C., the acid chloride which has precipitated in separated off by filtration and recrystallised from cyclohexane (20 g of acid chloride/500 ml of cyclohexane).

Yield: 39.3 g (80.2% of theory); melting point 115.5°–116.5° C.

Analysis for $C_{14}H_9Cl_2NO_4$ (molecular weight 326.138): calculated: C 51.56%, H 2.78%, N 4.29%, Cl 21.74%: found: C 51.5%, H 2.9%, N 4.4%, Cl 21.6%.

EXAMPLE 35

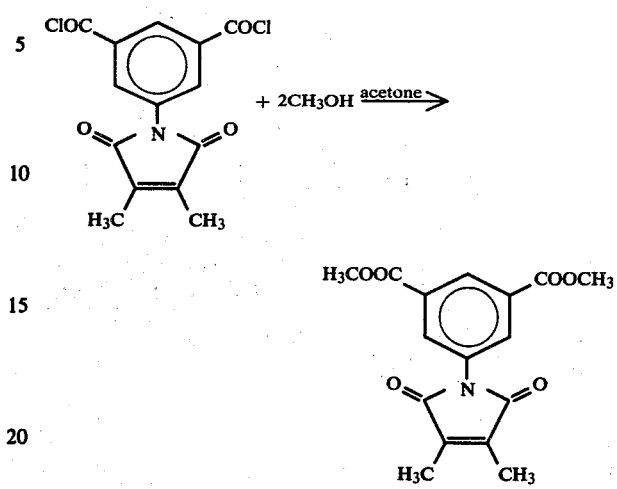

47.2 g (0.145 mol) of 5-dimethylmaleimidyl-isophthalic acid dichloride are dissolved in 94.4 g of dry acetone. This solution is boiled under reflux; whilst boiling, 1 liter of dry methanol is gradually added dropwise. A white product precipitates out. When the addition is complete, the reaction mixture is cooled to about 20°–25° C. and the residue is filtered off. After drying, 45.6 g (99% of theory) of pale yellowish crystals of the above diester are obtained; melting point 229°–234° C. (recrystallised from diethyl ketone and sublimed).

$H^1$ NMR: (DMSO-$d_6$, TMS=0) 6H at 1.96 ppm (methyl protons).

Analysis for $C_{16}H_{15}NO_6$ (molecular weight 317): calculated: C 60.56%, H 4.75%, N 4.41%: found: C 61.0%, H 4.8%, N 4.7%.

EXAMPLE 36

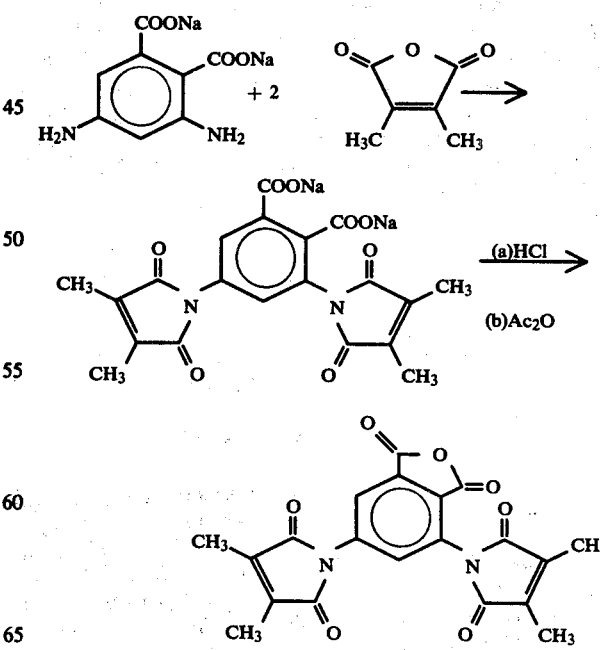

7.20 g (0.039 mol) of disodium 3,5-diaminophthalate, dissolved in 200 ml of water, are added to a solution of 8.82 g (0.078 mol) of dimethylmaleic anhydride in 80 ml of toluene. This mixture is boiled under reflux for 1 hour. It is then evaporated to dryness in a rotary evaporator, the residue is dissolved, at 90° C., in 100 ml of N,N-dimethylacetamide and 50 ml of water and the solution is rendered acid to Congo Blue with 10% strength hydrochloric acid. After cooling, the slurry-like mixture is filtered and the residue is rinsed with acetone and then dried in vacuo at 80° C. The dry residue is then suspended in 100 ml of acetic anhydride and this mixture is warmed to about 100° C. for 1 hour. It is then evaporated to dryness and the residue is recrystallized from 1,2-dichlorobenzene. 8.9 g (69% of theory) of 3,5-bis-(dimethylmaleimidyl)-phthalic anhydride are obtained; colour: light brownish; melting point 298° C. (decomposition).

H¹ NMR: (DMSO-d₆, TMS=0) 2H (aromatic) 7.94 and 7.98 ppm, 12H (methyl protons 1.98 ppm).

Analysis for $C_{20}H_{14}N_2O_7$ (molecular weight 394.12): calculated: C 60.92%, H 3.58%, N 7.11%: found: C 60.67%, H 4.44%, N 7.32%.

EXAMPLE 37

27.1 g (0.1 mol) of 3-dimethylmaleimidyl-phthalic anhydride and 13 g (0.1 mol) of freshly distilled 2-hydroxyethyl methacrylate are dissolved in 500 ml of tetrahydrofurane. About 0.5 ml of triethylamine and 0.05 g of hydroquinone are added to this solution. The reaction mixture is now stirred for 24 hours at 50° C. and under dry nitrogen. When the reaction has ended, the solvent is evaporated off by means of a rotary evaporator. The resulting oil is taken up in 500 ml of diethyl ether and the ether solution is washed, first with 100 ml of 0.5 N sodium hydroxide solution and then with twice 200 ml of water. The ether solution is then evaporated, the above imidyl derivative (N-[2,3-dicarboxyphenyl-3-(5-methyl-3-oxa-4-oxo-hex-5-enyl) ester]-dimethyl-maleimide) being obtained in 98% yield; $n_{40}^d = 1.5155$.

Analysis for $C_{20}H_{19}NO_8$ (molecular weight 401): calculated: C 59.85%, H 4.72%, N 3.49%: found: C 60.3%, H 5.8%, N 3.5%.

NMR spectrum (CDCl₃): δ=1.98 ppm (methyl protons).

EXAMPLE 38

48.3 g (0.1 mol) of the 5-dimethylmaleimidyl-trimellitic anhydride-lauryl ester prepared according to Example 32 and 13 g (0.1 mol) of freshly distilled methacrylic acid 2-hydroxyethyl ester are dissolved in 500 ml of tetrahydrofurane. About 0.5 ml of triethylamine and 0.05 g of hydroquinone are added to this solution. The mixture is now stirred for 24 hours at 50° C. and under dry nitrogen. When the reaction has ended, the solvent is evaporated off by means of a rotary evaporator. The resulting oil is taken up in 500 ml of ether and the ether solution is washed first with 100 ml of 0.5 N sodium hydroxide solution and then with twice 200 ml of water. The ether solution is then evaporated, 60 g (98% of theory) of the above imidyl derivative (=N-(2,3,5-tricarboxyphenyl-3-{-5-methyl-3-oxa-4-oxo-hex-6-enyl}-5-[dodecyl]diester)-dimethylmaleimide) being obtained in the form of a pale yellowish, highly viscous oil; $n_{20}^d = 1.5046$.

Analysis for $C_{27}H_{33}O_7N$ (molecular weight 483): calculated: C 64.59%, H 7.06%, N 2.28%: found: C 64.33%, H 7.61%, N 2.45%.

NMR spectrum (CDCl₃): δ=1.98 ppm (methyl protons).

EXAMPLE 39

The 3,5-(bis-dimethylmaleimidyl)-phthalic anhydride obtained according to Example 36 is reacted with freshly distilled methacrylic acid 2-hydroxyethyl ester, in a manner analogous to that described in Example 38. 98% of theory of the compound of the formula are obtained; melting point 42° C.

Analysis for $C_{26}H_{24}O_{10}N_2$ (molecular weight 542): calculated: C 59.5%, H 4.7%, N 5.3%: found: C 59.3%, H 4.9%, N 5.1%.

NMR spectrum (CDCl₃): δ=1.98 ppm (methyl protons).

EXAMPLE 40

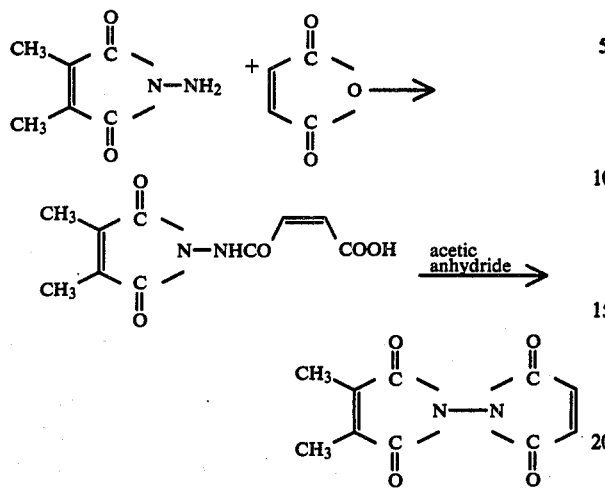

49 g (0.5 mol) of maleic anhydride, dissolved in 400 ml of diethyl ether, are added, in the course of about 10 minutes, whilst stirring, to 70 g (0.5 mol) of N-amino-dimethylmaleimide, dissolved in 200 ml of methylene chloride, the mixture is stirred overnight at about 20°-25° C. and the resulting precipitate is filtered off and dried (in vacuo at 60° C. for 2 hours). 107 g (90% of theory) of white amide-acid are obtained; melting point 167°-168° C.

Analysis for $C_{10}H_{10}N_2O_5$ (molecular weight 238.20): calculated: C 50.43%, H 4.23%, N 11.76%: found: C 50.59%, H 4.30%, N 11.90%.

9.6 g (0.040 mol) of this amide-acid are stirred with 40 ml of acetic anhydride at 80° C. until everything has gone into solution (about 20 minutes). The solution is concentrated well, at 60° C./15 mm Hg, in a rotary evaporator. 9.6 g of a crude product remain and can be purified by recrystallisation from methanol or by sublimation at 110° C./0.1 mm Hg. After purification, 7.9 g (90% of theory) of white N-dimethylmaleimido-maleimide are obtained; melting point 116°-120° C.

Analysis for $C_{10}H_8N_2O_4$ (molecular weight 220.18): calculated: C 54.55%, H 3.66%, N 12.73%: found: C 54.55%, H 3.68%, N 13.07%.

EXAMPLE 41

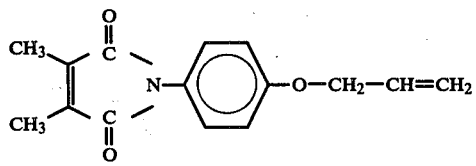

70.0 g (0.31 mol) of the N-(4-hydroxyphenyl)-dimethylmaleimide obtained according to Example 13 are dissolved in 500 ml of acetone. 41.0 ml (0.58 mol) of allyl bromide and 44.2 g of potassium carbonate are then added; the reaction mixture is warmed to 55°-58° C. and kept at this temperature for 4 hours, whilst stirring. The reaction mixture is then poured into 500 ml of ice/water. The N-(allyloxyphenyl)-dimethylmaleimide precipitates out in the form of pale yellow crystals. It is filtered off and dried in vacuo at 70° C.; melting point 122°-123° C.; yield 80.7 g=98% of theory.

EXAMPLE 42

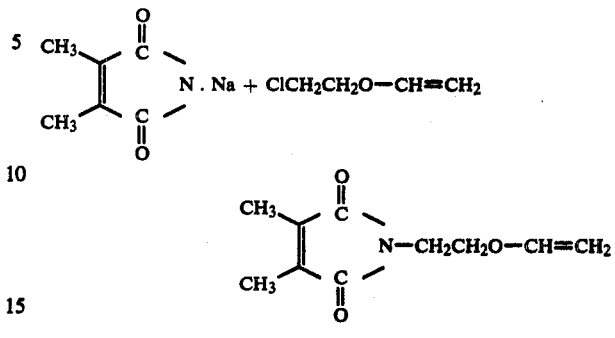

14.7 g (0.1 mol) of the sodium salt of dimethylmaleimide are introduced into 50 ml (0.5 mol) of 2-chloroethyl vinyl ether. After adding 0.5 g of methyltriethylammonium iodide, the mixture is warmed to 100°-105° C. and stirred at this temperature for 4 hours. The sodium chloride which has precipitated out is filtered off and the excess 2-chloroethyl vinyl ether is distilled off in vacuo. 18 g of a dark brown oil remain and this solidifies on cooling. For purification, the product is recrystallised from heptane; melting point 75° C.

EXAMPLE 43

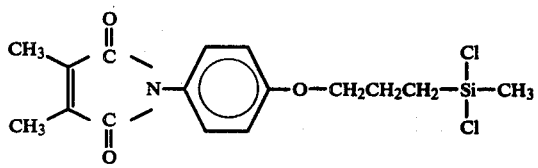

0.5 ml of a 1% strength solution of hexachloroplatinic acid in ethylene glycol dimethyl ether is added to a solution of 35 g (0.136 mol) of N-(4-allyloxyphenyl)-dimethylmaleimide (prepared according to Example 41) in 500 ml of toluene and a solution of 20 g (0.174 mol) of dichloromethylsilane in 100 ml of toluene is added dropwise to the resulting mixture at 105° C. and with the exclusion of moisture. The reaction mixture is stirred at 105°-110° C. for 3 hours and the solvent is then distilled off. Melting point 122°-123°.

Analysis: calculated: C 51.6%, H 5.2%, N 3.8%, Cl 19.0%, Si 7.6%: found: C 51.8%, H 5.3%, N 3.8%, Cl 18.6%, Si 7.7%.

EXAMPLE 44

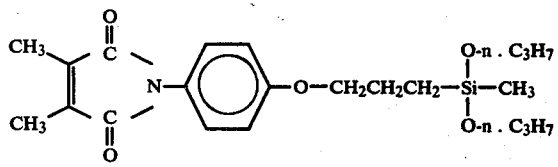

If, in place of 20 g of dichloromethylsilane, the equivalent amount of dipropoxymethylsilane is used and in other respects the procedure is as indicated in Example 43, dipropoxy-methyl-3-(4'-dimethylmaleimidylphenoxy)-propylsilane is obtained. For purification, the product is distilled under 0.001 mm Hg and at 198°-203° C.; melting point 87° C.

Analysis: calculated: C 63.0%, H 7.9%, N 3.3%, Si 6.7%: found: C 62.9%, H 8.0%, N 3.5%, Si 6.9%.

EXAMPLE 45

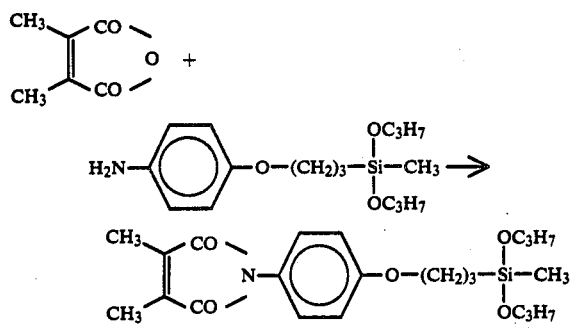

In accordance with the procedure described in Example 1, 12.61 g (0.1 mol) of dimethylmaleic anhydride are reacted, in the melt, with 31.15 g (0.1 mol) of the above aminosilane. The resulting oily, pale yellowish coloured product is distilled off.

Yield: 32.3 g (77% of theory);
Boiling point/$10^{-3}$ mm Hg: 192°-200° C.

Analysis for $C_{22}H_{33}N_1O_5Si_1$ (molecular weight 419.59): calculated: C 62.9%, H 7.9%, N 3.3%, Si 6.6%: found: C 62.7%, H 8.1%, N 3.4%, Si 6.9%.

The dipropoxy-methyl-3-(4'-dimethylmaleimidyl-phenoxy)-propylsilane obtained according to the above example can be converted into the corresponding dichloro-methyl-3-(4'-dimethylmaleimidyl-phenoxypropylsilane of the formula

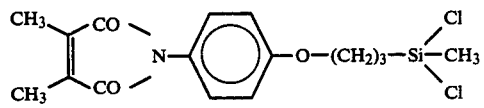

by reaction with suitable chlorinating agents, such as thionyl chloride or polyacrylic acid chloride.

The aminosilane used in the above example is obtained in a manner which is in itself known by an addition reaction or methyl-di-n-propoxysilane with 4-allyloxyaniline at about 100° C. in the presence of $H_2PtCl_6$ as the catalyst.

EXAMPLE 46

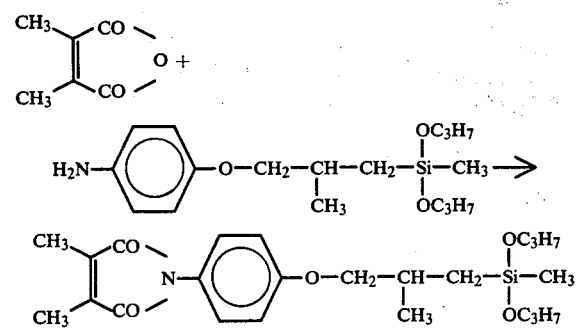

In accordance with the procedure described in Example 1, 12.61 g (0.1 mol) of dimethylmaleic anhydride are reacted in the melt with 32.55 g (0.1 mol) of the above aminosilane. The resulting oily, pale yellowish product is distilled off.

Yield: 38.6 g (80% of theory);
Boiling point/$10^{-3}$ mm Hg: 200°-205° C.

Analysis for $C_{23}H_{35}N_1O_5Si$ (molecular weight 433.62): calculated: C 63.71%, H 8.14%, N 3.23%, Si 6.48%: found: C 63.5%, H 8.3%, N 3.5%, Si 6.5%.

The compound of the formula

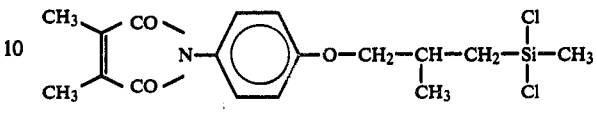

is obtained by reacting the product with thionyl chloride or polymethacrylic acid chloride.

The aminosilane used in the above example is obtained in a manner which is in itself known by an addition reaction of methyl-di-n-propoxysilane with 4-methallyloxysilane at about 100° C. in the presence of $H_2PtCl_6$ as the catalyst.

The dimethylmaleimidyl derivatives described above can also be obtained in comparable yields by an addition reaction of methyl-di-n-propoxysilane or methyldichlorosilane with the dimethylmaleimidyl derivative of the formula

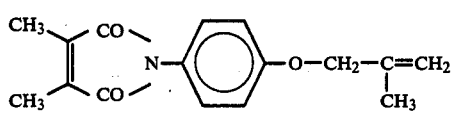

The addition reaction is carried out, for example, in boiling toluene and using $H_2PtCl_6$ as the catalyst.

In the above Examples 45 and 46 it is also possible to employ equivalent amounts of the corresponding 3-aminosilanes or mixtures of 3- and 4-aminosilanes in place of the 4-aminosilanes described.

EXAMPLE 47

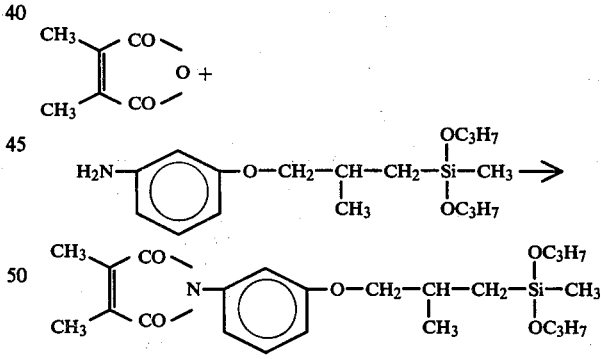

In accordance with the procedure described in Example 1, 12.61 g (0.1 mol) of dimethylmaleic anhydride are reacted in the melt with 32.55 g (0.1 mol) of the above aminosilane. The oily, pale yellow coloured product is distilled off.

Yield 32.6 g (75% of theory); boiling point/$10^{-3}$ mm Hg: 200°-205° C.

Analysis for $C_{23}H_{35}N_1O_5Si$ (molecular weight 433.62): calculated: C 63.71%, H 8.14%, N 3.23%, Si 6.46%: found: C 63.1%, H 7.9%, N 3.5%, Si 6.7%

The above dimethylmaleimidyl derivative can also be manufactured by an addition reaction of methyl-di-n-propoxysilane with the dimethylmaleimidyl compound of the formula propoxysilane or methyl-dichlorosilane with the compound of the formula

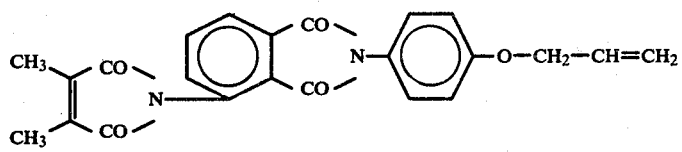

EXAMPLE 49

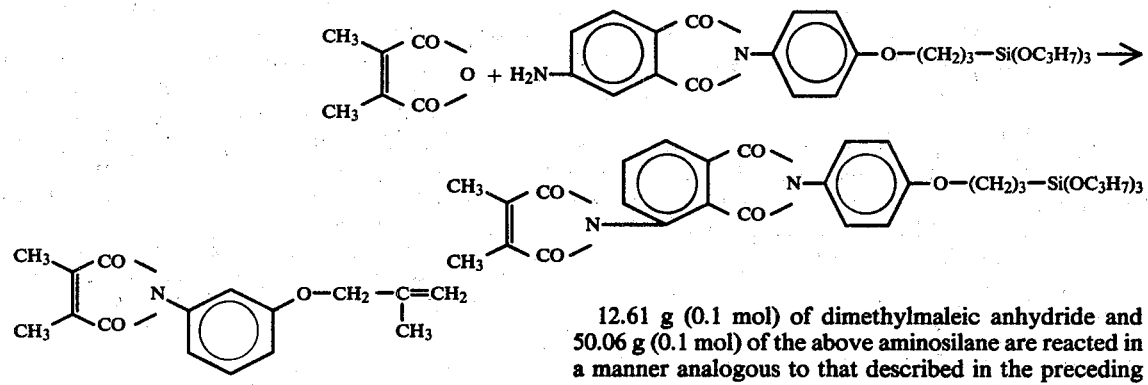

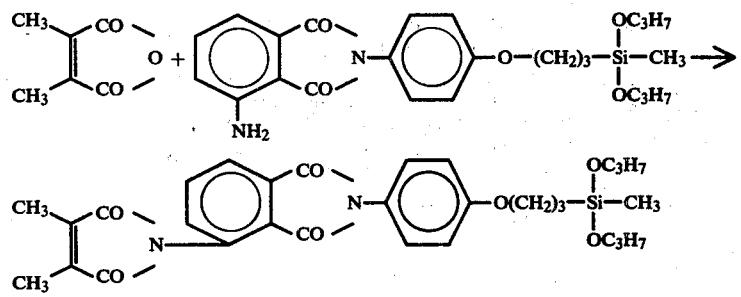

in boiling toluene and using $H_2PtCl_6$ as the catalyst.

EXAMPLE 48

12.61 g (0.1 mol) of dimethylmaleic anhydride and 50.06 g (0.1 mol) of the above aminosilane are reacted in a manner analogous to that described in the preceding Examples 45–47. The resulting solid, yellow coloured reaction product is recrystallised from a 1:3 mixture by volume of dibutyl ether/hexane; melting point 110° C.

12.61 g (0.1 mol) of dimethylmaleic anhydride are reacted, in the manner described in the preceding Examples 45–47, with 42.85 g (0.1 mol) of the above aminosilane. The resulting solid, yellow coloured reaction product is recrystallised from a 1:1 mixture by volume of dibutyl ether/hexane; melting point 106°–108° C.

Analysis for $C_{30}H_{36}N_2O_7Si_1$ (molecular weight 564.71): calculated: C 63.8%, H 6.4%, N 5.0%, Si 5.0%: found: C 63.4%, H 6.4%, N 5.2%, Si 5.1%:

The compound of the formula

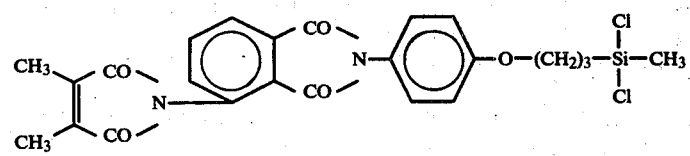

is obtained by reacting the product with thionyl chloride or polyacrylic acid chloride.

The above dimethylmaleimidyl derivatives can also be obtained by an addition reaction of methyl-di-n-

EXAMPLE 50

137.4 g (0.34 mol) of the dimethylmaleimidyl derivative obtained according to Example 37, together with 0.8 g of azo-isobutyronitrile, are dissolved in 625 ml of tetrahydrofurane. This mixture is polymerised for 5 hours under gentle reflux (about 80° C.), whilst stirring and continuously under a nitrogen atmosphere. When the reaction has ended, the reaction mixture is cooled to 20°–20° C. and the polymer is precipitated by adding the reaction solution dropwise to 5 liters of hexane. 120.7 g (88% of theory) of the polymer, which consists of structural elements of the formula

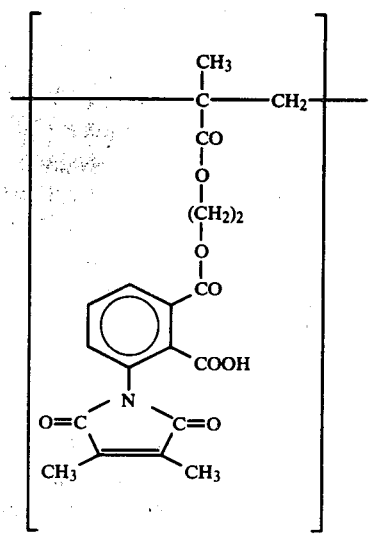

are obtained.

NMR (chlorobenzene, TMS-O): δ=1.96 ppm (methyl protons of the dimethylmaleimidyl radical); inherent viscosity 0.12 dl/g (0.5% strength solution in N,N-dimethylformamide, at 20° C.).

EXAMPLE 51

14.4 g (0.02 mol) of the dimethylmaleimidyl derivative obtained according to Example 38, together with 20 g (0.2 mol) of methacrylic acid methyl ester, 10 g (0.07 mol) of methacrylic acid 2-hydroxyethyl ester and 0.4 g of azo-isobutyronitrile, are dissolved in 270 ml of tetrahydrofurane. This mixture is polymerised under gentle reflux (about 80° C.), whilst stirring and continuously under a nitrogen atmosphere. When the reaction has ended (reaction time about 7 hours), the mixture is cooled to 20°-25° C. and the polymer is precipitated by adding the reaction solution dropwise to 2 liters of hexane. 27 g (60% of theory) of the polymer, which consists of structural elements of the formula inherent viscosity 0.19 dl/g (0.5% strength solution in N,N-dimethylformamide at 20° C.).

EXAMPLE 52

Copolyamide of

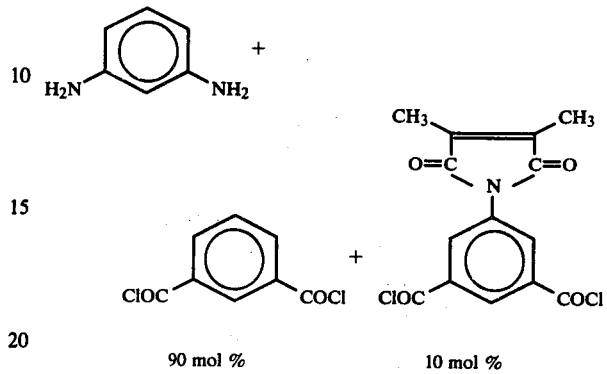

(a) Preparation of the acid chloride mixture (90:10 mol %)

40.20 g of isophthalic acid dichloride and 7.17 g of 5-dimethylmaleimidyl-isophthalic acid dichloride, prepared according to Examples 33/34, are melted together at 70° C., the melt is allowed to solidify and the solid is crumbled.

(b) Polycondensation 21.47 g of m-phenylenediamine are dissolved in 190 ml of N,N-dimethylacetamide, the solution is cooled to −25° C. using a bath of solid carbon dioxide and, whilst stirring vigorously and under an inert gas atmosphere, 43.07 g of the acid chloride mixture obtained according to (a) are added in the solid form. During the addition, the temperature rises to about +30° C. The cooling bath is removed and the reaction product is stirred for a further 3 hours at 20°-25° C. After diluting with 190 ml of N,N-dimethylacetamide, the polymer is precipitated, in a mixer, by means of water, washed with water until

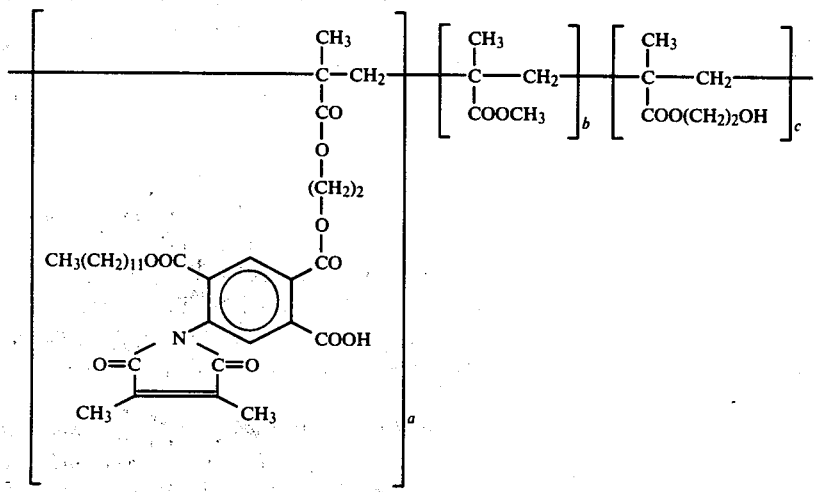

(a=32% by weight; b=46% by weight and c=22% by weight) are obtained.

NMR (chlorobenzene, TMS-O): δ=1.94 ppm (methyl protons of the dimethylmaleimidyl radical);

neutral and dried overnight at 120° C. in a vacuum drying cabinet. A fibrous, almost white polymer which has an inherent viscosity of 0.7 dl/g (0.5% strength solution in N,N-dimethylacetamide, measured at 25° C.), is soluble in N,N-dimethylformamide and N,N- dimethylacetamide without the addition of a salt and can be processed to films in a manner which is in itself known, is obtained in quantitative yield. The films can be crosslinked by irradiation with UV light, insoluble films being formed.

EXAMPLE 53

38.446 g (0.192 mol) of 4,4'-diaminodiphenyl ether are dissolved in 200 ml of anhydrous N,N-dimethylacetamide, under nitrogen. The solution is cooled to −15° C. A mixture of 15.00 g (0.048 mol) of 5-dimethylmaleimidyl-trimellitic anhydride-chloride and 30.322 g (0.144 mol) of trimellitic anhydride-chloride are sprinkled in at −15° C. to −5° C., whilst stirring vigorously. A slightly exothermic reaction takes place and a viscous solution is formed, which is diluted with 100 ml of N,N-dimethylacetamide and gradually warmed to 20°–25° C. After stirring for 2 hours at 20°–25° C. a further 100 ml of N,N-dimethylacetamide are added. The hydrochloric acid formed during the reaction is precipitated with 19.42 g (0.192 mol) of triethylamine. The salt which has precipitated out is filtered off. The resulting clear solution has an inherent viscosity of 0.65 dl/g (0.5% strength solution in N,N-dimethylacetamide at 25° C.).

The resulting polymer solution is suitable, if appropriate after the addition of a sensitiser, such as thioxanthone, for the manufacture of photochemically crosslinkable films and sheets, for example for photographic purposes. Films and sheets of this type can be obtained according to known methods, for example by casting, evaporating the solvent and cyclising the amide-acid to the amide-imide at elevated temperature in vacuo, and crosslinked by means of UV light to give products which are resistant to solvents.

The cyclised polymer which has not been crosslinked is soluble in N,N-dimethylformamide, N,N-dimethylacetamide, N-methyl-pyrrolidone and concentrated sulphuric acid.

EXAMPLE 54

Copolyamide of:

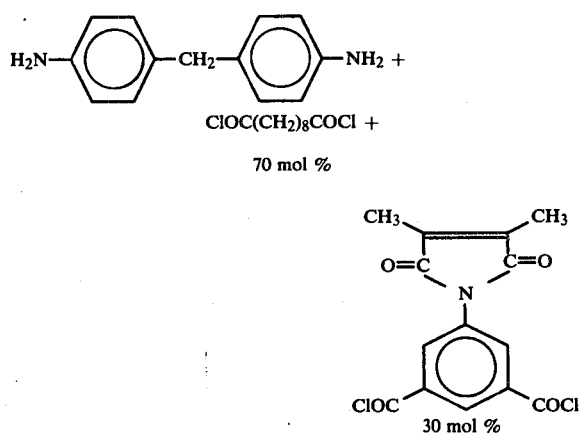

EXAMPLE 55

100 g of "Gantrez 119", which is a maleic anhydride copolymer consisting of structural elements of the formula

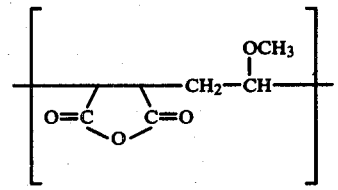

(anhydride content 0.64 mol %), and 82 g (0.66 mol) of the N-(4-hydroxycyclohexyl)-dimethylmaleimide prepared according to Example 1 are dissolved in 400 ml of dry tetrahydrofurane. 1 ml of concentrated sulphuric acid is then added. The reaction mixture is kept at 80° C. for 72 hours, whilst stirring. The resulting homogeneous solution is then poured into 1 liter of hexane. The precipitate which is deposited is separated off, washed several times with diethyl ether, dried at 40° C. in vacuo and ground to a powder.

EXAMPLE 56

Anodised aluminum plates are coated, by the whirler-coating process (2,000–3,000 revolutions/minute), with a 10% strength solution, in cyclohexanone, of the polymer obtained according to Example 55, which solution also contains 0.5% by weight of thioxanthone (sensitiser). The coated plates are dried at a temperature at about 30° C.

The plates treated in this way are exposed under a photographic step wedge (12 steps) for 10 seconds by the contact process using a 400 Watt mercury high-pressure lamp at a distance of 40 cm. The plates are then washed (fixed) with a 5% strength aqueous solution of NaHCO₃ and dyed with a 1% strength aqueous solution of the dyestuff of the formula

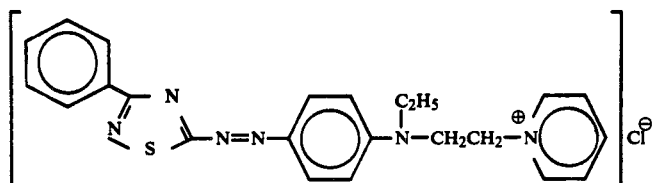

The plates are then washed with water for 2–3 seconds and dried. All of the parts with screen dots have been recorded. 10 wedge steps are clearly visible. Fixing, dyeing and washing can be carried out in a conventional roll processor.

EXAMPLE 57

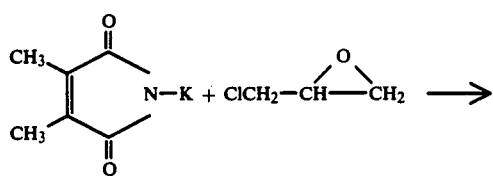

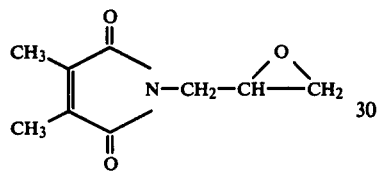

28 g (0.224 mol) of dimethylmaleimide are suspended in 600 ml of toluene, in a flask which is provided with a stirrer and a water separator, and the suspension is heated to the boil. 12.5 g (0.224 mol) of finely powdered potassium hydroxide are introduced in portions into the reaction mixture and the reaction mixture is boiled under reflux for a further 2 hours, the theoretical amount of water (about 4.5 ml) being separated off. The reaction mixture is then cooled and filtered and the residue (potassium salt of dimethylmaleimide) is washed with acetone and dried.

30 g (0.1.84 mol) of the above potassium salt of dimethylmaleimide and 0.05 g of tetramethylammonium chloride are suspended in 175 g (1.89 mol) of epichlorohydrin. The suspension is boiled under reflux for 18 hours, whilst stirring, and then filtered. The excess epichlorohydrin is removed from the filtrate by distillation under reduced pressure. 30 g of a viscous, pale brown liquid, which has an epoxide content of 4.9 equivalents/kg (calculated 5.5 equivalents/kg), are obtained. The NMR spectrum of the product obtained is compatible with that of N-glycidyl-dimethylmaleimide.

In the above example it is also possible to use the corresponding sodium salt in place of the potassium salt of dimethylmaleimide. This sodium salt is prepared as follows: 25.0 g (0.2 mol) of dimethylmaleimide are dissolved in 20 ml of methanol. 10.8 g (0.2 mol) of sodium methylate, dissolved in 100 ml of methanol, are than added dropwise to the reaction mixture at 20°–25° C., whilst stirring. After two hours 100 ml of acetone are added and the crystals which have precipitated are filtered off and dried.

Yield: 23.5 g (80% of theory) of the Na salt of dimethylmaleimide.

Analysis for $C_6H_6NO_2Na$ (molecular weight 147.1): calculated: Na 15.6%; found: Na 15.5%.

The NMR spectrum of the substance obtained is compatible with that of the sodium salt of dimethylmaleimide.

We claim:

1. A compound of the formula

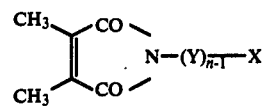

wherein
n is 1 or 2,
when n is 1, X represents -NHCO-alkenyl with 2 to 4 carbon atoms in the alkenyl group or a group of the formula

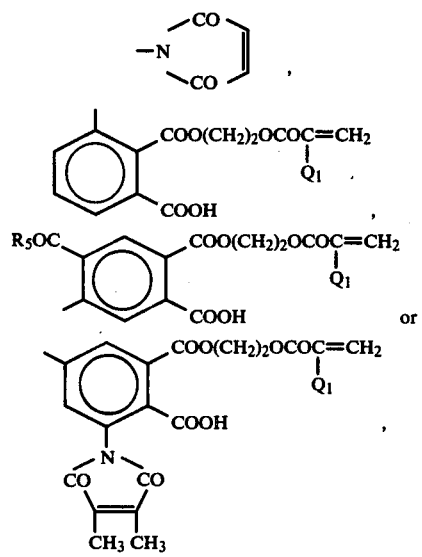

wherein $R_5$ is alkoxy having from 1 to 12 carbon atoms and $Q_1$ is hydrogen or methyl; and
when n is 2, Y represents alkylene having 2 to 6 carbon atoms or phenylene, and X is -O-alkenyl having 2 to 4 carbon atoms.

2. A compound according to claim 1 wherein n is 1 and X is $-NHCOC(CH_3)=CH_2$.

3. A compound according to claim 1 wherein n is 1, $R_5$ is dodecyl and $Q_1$ is methyl.

4. A compound according to claim 1 wherein n is 2, Y is ethylene or phenylene and X is -O-allyl, -O-vinyl or -O-methallyl.

5. A compound

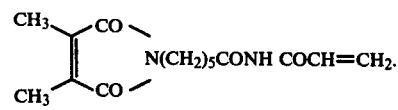

$(CH_2)_5CONH\ COCH=CH_2$.

* * * * *